(12) United States Patent
David

(10) Patent No.: US 6,842,722 B2
(45) Date of Patent: Jan. 11, 2005

(54) PHYSIOLOGICAL MEASURING SYSTEM COMPRISING A GARMENT IN THE FORM OF A SLEEVE OR GLOVE AND SENSING APPARATUS INCORPORATED IN THE GARMENT

(76) Inventor: Daniel David, 52 Hashalom St., Ranana (IL)

( * ) Notice: Subject to any disclaimer, the term of this patent is extended or adjusted under 35 U.S.C. 154(b) by 3 days.

(21) Appl. No.: 10/324,303

(22) Filed: Dec. 20, 2002

(65) Prior Publication Data

US 2003/0088385 A1 May 8, 2003

Related U.S. Application Data

(63) Continuation of application No. 10/117,250, filed on Apr. 5, 2002, now Pat. No. 6,516,289, and a continuation of application No. 09/359,340, filed on Jul. 21, 1999, now abandoned.

(51) Int. Cl.[7] .................................................. A61B 5/00
(52) U.S. Cl. ........................ 702/189; 128/639; 128/642; 128/666; 128/903; 600/300; 600/384
(58) Field of Search .......................... 702/189; 128/639, 128/666, 903, 904; 600/300, 301, 302; 604/66, 67, 340, 481, 482

(56) References Cited

U.S. PATENT DOCUMENTS

| | | | |
|---|---|---|---|
| 4,572,197 A | | 2/1986 | Moore et al. |
| 4,854,323 A | | 8/1989 | Rubin |
| 4,920,969 A | | 5/1990 | Suzuki et al. |
| 5,072,458 A | | 12/1991 | Suzuki |
| 5,353,793 A | * | 10/1994 | Bornn .......................... 600/386 |
| 5,465,727 A | | 11/1995 | Reinhold, Jr. |
| 5,511,546 A | | 4/1996 | Hon |
| 5,724,025 A | | 3/1998 | Tavori |
| 5,748,367 A | | 5/1998 | Lucke et al. |
| 6,248,064 B1 | * | 6/2001 | Gopinathan et al. ........ 600/300 |
| 6,516,289 B2 | * | 2/2003 | David .......................... 600/384 |

* cited by examiner

*Primary Examiner*—John Barlow
*Assistant Examiner*—John Le
(74) *Attorney, Agent, or Firm*—Banner & Witcoff, Ltd.

(57) ABSTRACT

A measuring system for measuring physiological parameters comprises a garment in the form of a sleeve or glove, or combination sleeve and glove, having a series of sensors and a control unit incorporated therewith. The control unit sleeve or glove and a sling in combination with the measurement of numerous physiological parameters by effecting accurate placement of the sensors on a patient's body.

5 Claims, 7 Drawing Sheets

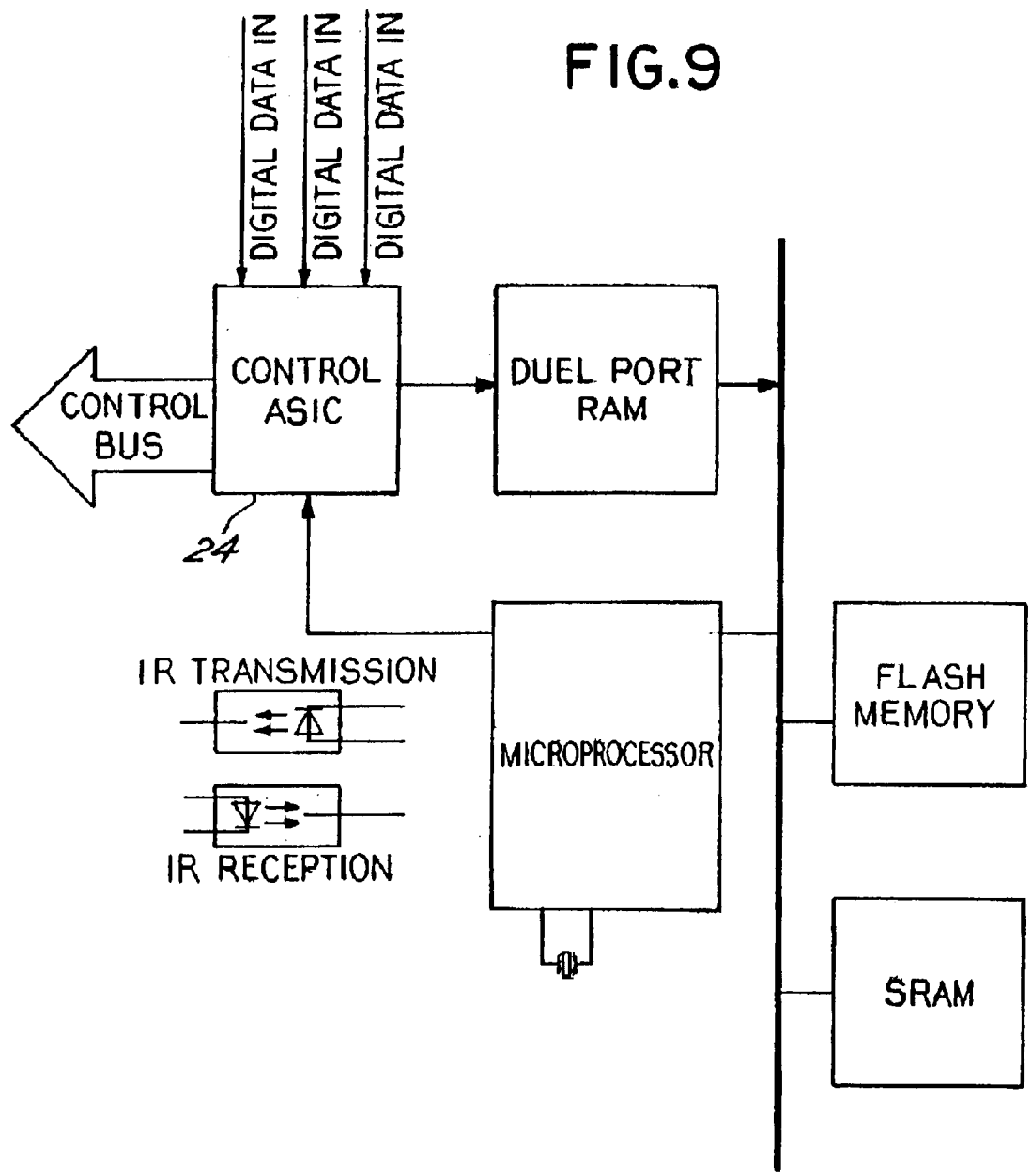

PHYSIOLOGICAL MEASURING SYSTEM COMPRISING A GARMENT IN THE FORM OF A SLEEVE OR GLOVE AND SENSING APPARATUS INCORPORATED IN THE GARMENT

CROSS REFERENCE TO RELATED APPLICATION

This is a continuation application of continuation application Ser. No. 10/117,250 filed Apr. 5, 2002 (now U.S. Pat. No. 6,516,289) which is based upon prior utility application Ser. No. 09/359,340 filed Jul. 21, 1999 now abandoned which is incorporated herewith by reference and for which priority is claimed.

BACKGROUND OF THE INVENTION

The field of the invention is in the design of devices for the acquisition, storage and transmission of multiple physiological parameters from human subjects to be monitored in hospitals, clinics, doctor's offices as well as in remote locations (home environment, work place, recreational activity, etc.) or unnatural environments (under-water, outer space, etc.).

The conventional acquisition of a human electrocardiogram (ECG) requires the recording of the time dependent fluctuations in the cardiac electrical activation from 12 different angles on the human torso (6 in the frontal plane and 6 in the horizontal plane) the so-called 12 lead ECG. Classically, this procedure involves the placement on the human body of at least 10 electrodes at various predefined anatomical locations.

Deviation from the predefined, worldwide, conventional localization of these electrodes may result in the acquisition of false data, possibly leading to misinterpretation and misdiagnosis. Even in the hospital or clinic environment, the correct and stable placement of the ECG electrodes, specifically the "chest leads" or "V leads" is often problematic, unless one applies six adhesive electrodes on the patient's chest. This is an impractical method in many circumstances due mainly to financial and patient inconvenience considerations. This problem is amplified in the attempts to record a full diagnostic 12 lead ECG in a remote location since the correct positioning of the electrodes by the examinee himself or by available laymen bystanders (family members, friends, etc.) is usually difficult and unreliable and therefore impractical.

To overcome this problem and to allow for the accurate acquisition of a 12 lead ECG in the ambulatory environment, various devices were conceived. Such devices include various forms of vests, girdles, adhesive and non-adhesive patches and other devices with incorporated electrodes allowing for the placement of the ECG electrodes on the patient's chest. However, most of these devices are cumbersome to use and have therefore not been universally accepted. Moreover, these devices do not lend themselves to the integration of other sensors and instrumentation for the simultaneous acquisition of other important physiological data (blood pressure, SpO2, etc.), such data being very useful for the purpose of ambulatory telemedical follow-up of patients in their own environment (home, workplace, recreational activity, etc).

SUMMARY OF THE INVENTION

The invention proposes to integrate a multitude of sensors and measuring devices in a garment in the form of a glove or sleeve for repeated continuous and simultaneous assessment of various physiological data such as ECG, noninvasive blood pressure (NIBP), blood oxygen saturation (SpO2), skin resistance, motion analysis, an electronic stethoscope, etc. An important advantage of the glove or sleeve is that it provides accurate, repeatable and conventional placement or localization of the ECG electrodes (specifically for the recording of the chest or V leads) by positioning the left arm of patient in a natural and very comfortable manner on the chest. Moreover, the glove or sleeve provides a means for simultaneous recording, storage and transmission of a multitude of other physiological data without the need for difficult manipulations. Furthermore, the incorporation of various measuring tools or instruments into one device, i.e. glove or sleeve, allows for the reciprocal calibration and easy acquisition of important, integrated, physiological data, a feature presently almost unavailable in the ambulatory environment (e.g. beat to beat NIBP changes, integration of: heart rate, blood pressure, skin resistance and other parameters for the assessment of autonomic balance, etc.).

Thus, it is an object of the invention to provide a system and method for repeatably and accurately positioning physiological sensors on a patient.

Another object is to provide a glove or sleeve with medical instrumentation and a protocol to position the glove or sleeve and thus the instrumentation on a patient.

These and other objects, advantages and features will be set forth in the description which follows.

BRIEF DESCRIPTION OF THE DRAWING

In the detailed description which follows, reference will be made to the drawing comprised of the following figures:

FIG. 9 is a schematic circuit diagram for the overall system.

DESCRIPTION OF THE PREFERRED EMBODIMENTS

General Description

Figure 5:
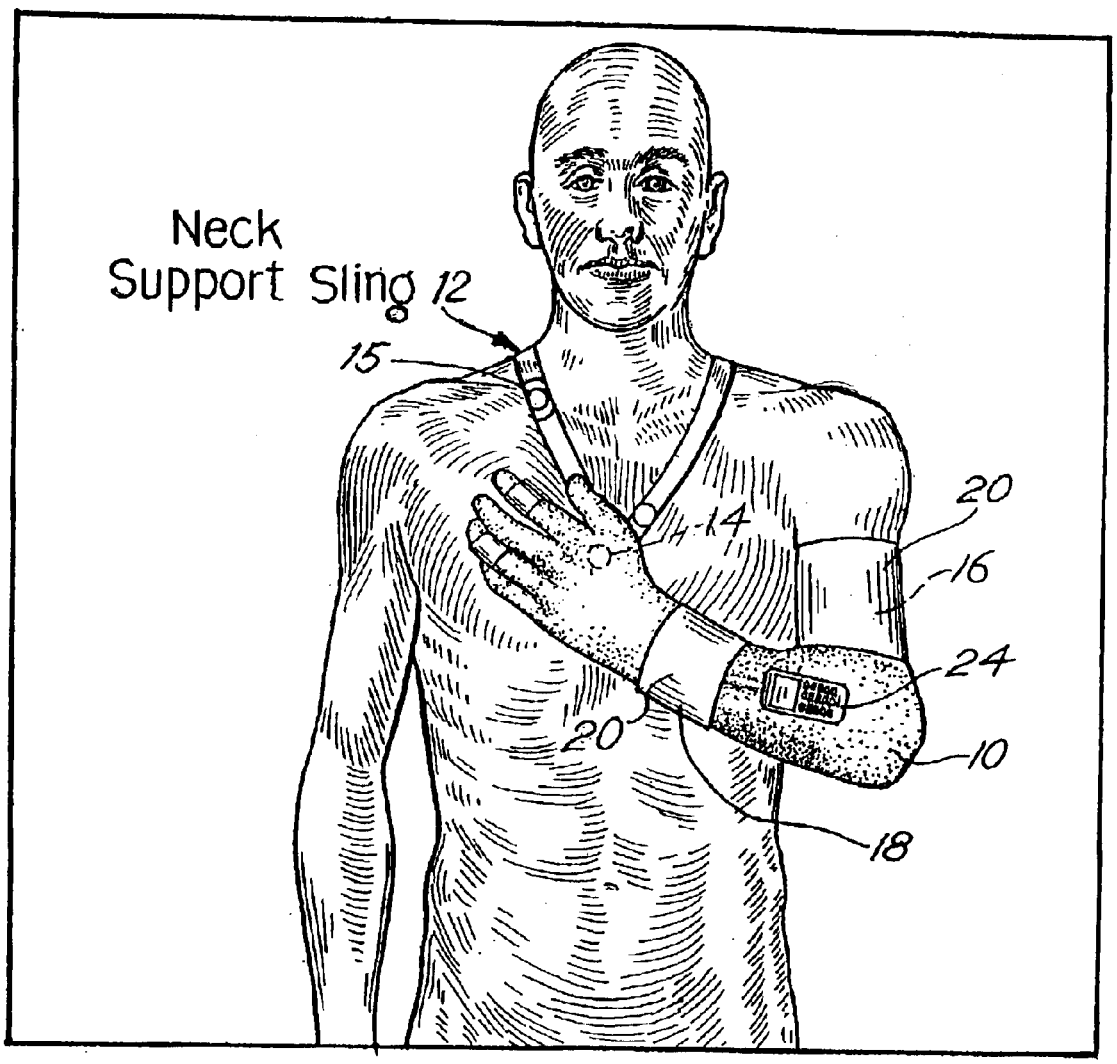
FIG. 5 depicts the advised positioning of the patient's left arm with the glove or sleeve device on the patient's chest to ensure proper localization of the 12 lead ECG electrodes for accurate and reproducible 12 lead ECG recordings, as well as the proper positioning of an electronic stethoscope. This arm position, aided by a neck sling which may also contain an additional ECG electrode, is natural and comfortable and therefore allows for prolonged, stable and continuous monitoring of all desired physiological parameters.

As depicted in FIGS. 2–5, the garment of the invention is preferably in the form of a glove or sleeve or combined glove and sleeve 10 and is fabricated from flexible material such as a nylon fabric that can fit snugly, without causing discomfort, on a human hand, forearm and arm. The glove or sleeve 10 is sized to fit or conform to patient arm size and shape. A neck sling 12 is attached to the glove or sleeve 10. The neck sling 12 is also adaptable and adjustable to the individual patient to ensure accurate positioning or elevation of the left arm on the chest of the patient for the proper placement of the ECG electrodes. Moreover, the neck sling 12 may include an additional ECG electrode 14 (FIG. 5).

Non-Invasive Blood Pressure

Two blood-pressure cuffs 16, 18 are incorporated in the glove or sleeve 10. One cuff 16 is positioned on the arm in the conventional blood-pressure measuring location, the second cuff 18 is placed on the forearm. Special restraining straps 20 mounted on the outside of the glove are wrapped around the blood-pressure cuffs 16, 18 to allow proper restrainment during cuff inflation. The blood-pressure cuffs 16, 18 are connected by a flexible tube 22, 23 to a central control unit or device 24 for inflation, deflation, and measurement of blood pressure by conventional methodology and used in the automatic determination of NIBP.

ECG

Figure 3:
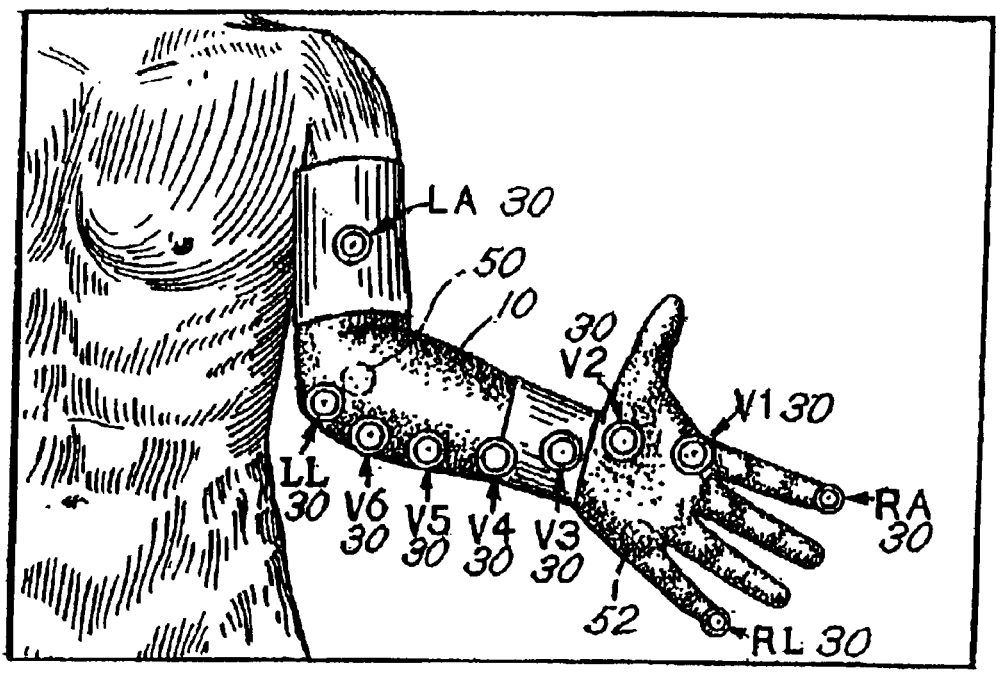
FIG. 3 depicts the ventral aspect of the glove or sleeve device illustrating the suggested location of the various ECG electrodes to permit easy placement of the ECG electrodes at predefined locations on a patient's body for recording a diagnostic 12 Lead ECG. Furthermore, two small microphones are depicted on the ventral side of the glove to be connected with the electronic stethoscope located in the central control unit.
Figure 4:
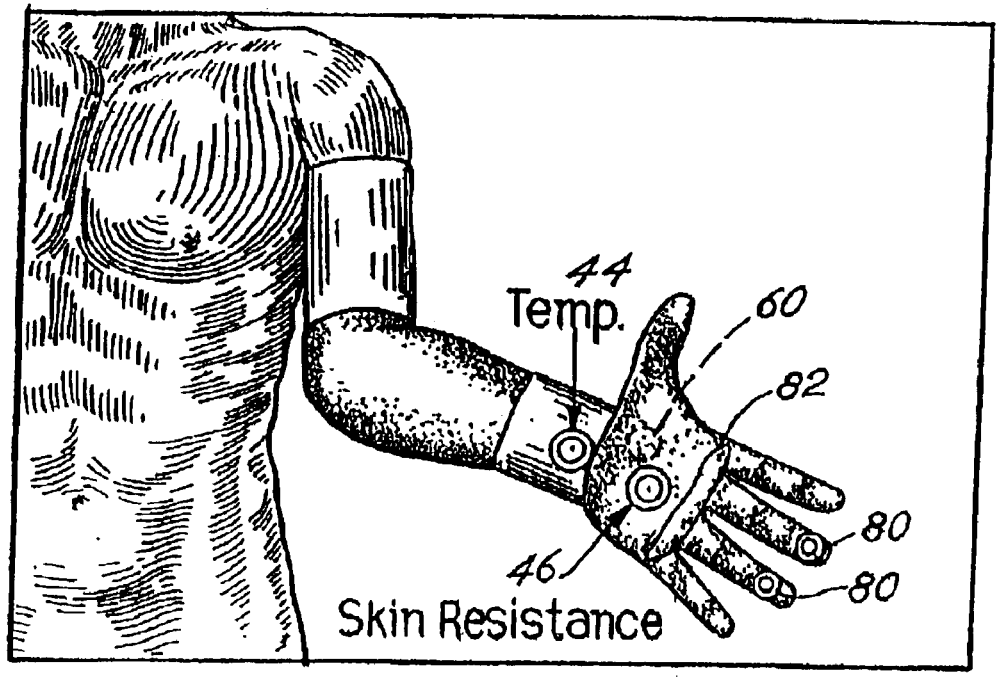
FIG. 4 depicts the ventral aspect of the glove or sleeve device depicting mainly the suggested location of other possible sensors for the determination of other physiological data such as temperature, skin resistance, etc.

At least ten ECG electrodes 30 are attached to the glove or sleeve 10 as depicted in FIG. 3. All of the ECG electrodes 30 except the LA electrode face the patient's chest whereas the LA electrode 30 is in contact with the skin of the left upper arm. The RA electrode 30 or it's equivalent is placed either on the index finger of the glove 10 in the neck sling 12, or in another suitable position. All of the electrodes 30 are wire connected to the ECG recording device located in the central control unit 24 retained in the sleeve 10.

The ECG electrodes 30 include the following features:

1. An automatic electrolyte solution application device. In the course of the recording of a conventional ECG, it is the routine to manually apply an electrolyte solution or cream to the contact surface between the skin and the recording electrodes to cause a reduction of skin resistance and to improve the conduction of the electrical current between the skin and the according electrode. In the described glove or sleeve 10, each electrode 30 includes means for automatic injection of an electrolyte solution into each electrode 30 prior to the acquisition of the ECG. This is achieved by connection of each electrode to an electrolyte reservoir by means of connecting tubes 32. Prior to the acquisition of the ECG recording, the electrolyte solution will be automatically sprayed into the electrodes 30 by pressure provided by a pump located in the central control unit 24.
2. A suction device for better electrode-skin contact: The ECG electrodes 30 will be configured as suction electrodes 30 and will be connected via suction tubes 34 to a pump located in the central control unit 24. Once the glove or sleeve 10 is placed on the chest in the proper position, an external signal will activate the pump to create the needed negative pressure and suction to maintain the proper electrode-skin contact. Following the termination of the ECG recording, the negative pressure will be abolished allowing detachment of the electrodes from the patient's chest. The same or separate pumps may be utilized to effect electrolyte application and the creation of electrode suction.

Non-Invasive Blood Oxygen Saturation (SpO2) Measuring Device

A conventional IR SpO2 measuring device 36 is incorporated in the glove or sleeve 10 and placed on one of the glove finger tips 38 to fit the patient's finger. Blood SpO2 is determined using the conventional methods applied for this measurement and the results will be stored in the central control unit 24.

Plethysmographic Beat To Beat NIBP Determination

A conventional finger Plethysmographic-measuring device 38 is incorporated in one of the glove fingertips 40 to fit on the patient's finger. An external restraining device 42 ensures continuous snug contact with the finger to provide continuous beat to beat changes in finger blood volume variation. The finger plethysmograph is wire connected to the central control unit 24. The signal is periodically calibrated using the conventional cuff blood pressure measurements thereby allowing for continuous beat to beat blood pressure monitoring.

Body Temperature

A thermistor 44 is incorporated in the glove or sleeve 10 and located on the ventral surface of the arm in direct contact with the skin to allow the determination of skin temperature. The thermistor 44 is wire connected to the central control unit 24.

Skin Resistance

A conventional sensor 46 for the determination of skin resistance is incorporated in the glove or sleeve I0 and wire connected to the central control unit 24.

Electronic Stethoscope

Two special microphones 50, 52 are attached to the ventral aspect of the glove or sleeve 10, one located over the base of the left lung and the second on one of the fingers for the simultaneous auscultation of both lungs. Furthermore, the finger microphones 50, 52 can also be moved to enable auscultation of the heart and other organs. The microphones 50, 52 will be connected to the central control unit 24 for recording and transmission of the auscultatory findings.

Motion and Force Measuring Sensors

Motion and force assessment devices 60, 80, 82 are incorporated in the glove or sleeve 10 mainly for the early detection of neurological and neuromuscular dysfunction. Sensors 60 assess passive and active functions such as:

1. Force of muscular contraction (e.g., handgrip, arm flexion and extension, etc.)
2. Passive pathological arm and finger motion (Parkinsonian tremor, flapping tremor, etc.).

3. Assessment of active finger, hand or arm motion (rapid hand pronation and supination, rapid finger motion, etc.).

Central Control Unit

Figure 1:
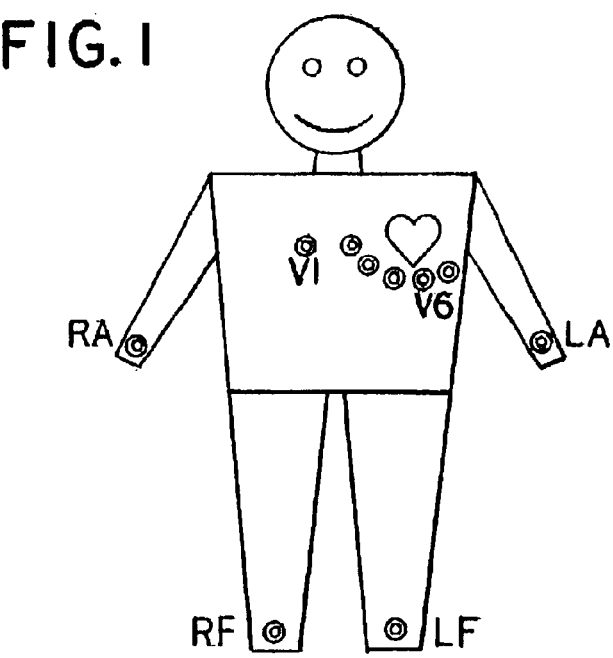
FIG. 1 depicts the classic locations for the placement of ECG electrodes on a human body for recording of a conventional 12-lead electrocardiogram.
Figure 2:
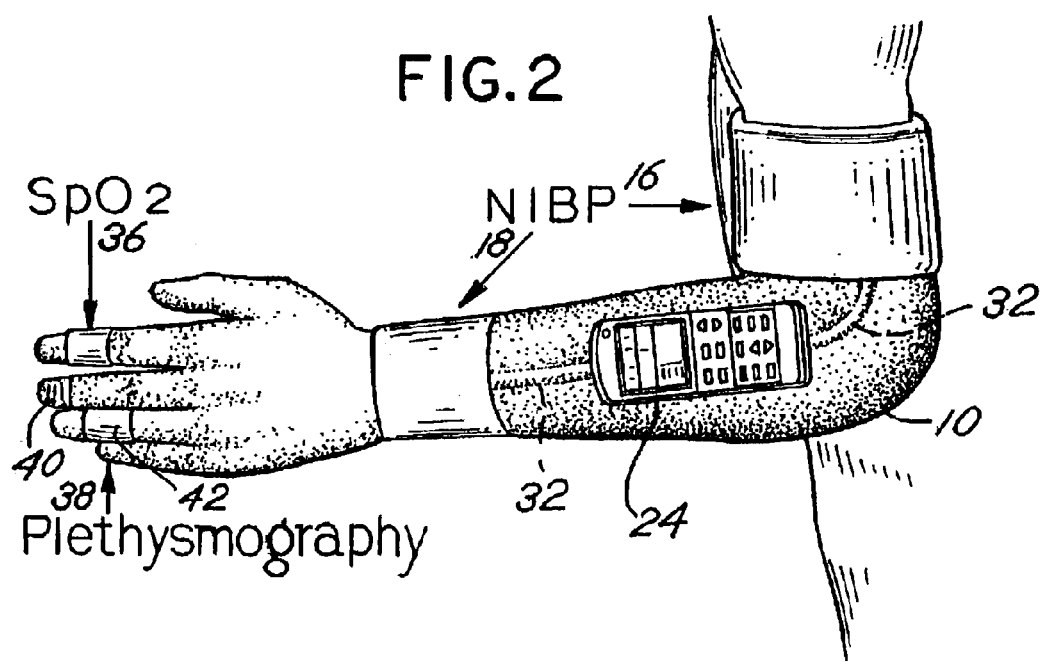
FIG. 2 depicts the central unit that includes all of the control functions for the various devices incorporated in the glove or sleeve device of the invention as well as on-line storage, analog to digital conversion and transmission capabilities of all acquired data; two bloodpressure cuffs (wrist and arm); and SpO2 and plethysmographic sensors (fingers).

The glove or sleeve 10 is equipped with a central control unit 24 attached to the dorsal aspect of the glove or sleeve 10 (FIG. 2). The general function of this unit 24 is the collection, transformation, storage and transmission of all of the physiological data collected from the various devices incorporated in the glove 10. Moreover, the central control unit 24 includes mechanical and other devices such as pumps, injectors, etc., needed for the proper functioning of the incorporated devices as described herein.

Specifically, the central control unit 24 includes the appropriate measuring element for each sensor. The measured data is digitized, stored and upon demand, made available for transmission by RF or IR or any other form of wireless telemetric transmission to a remote surveillance center. Conversely, the central control unit 24 has the ability to receive signals from a remote surveillance center for the activation or deactivation and other control functions of the various measuring devices incorporated in the glove 10.

In review, the glove 10 provides an unobtrusive stable platform for self-application of numerous physiological sensors using a glove and/or sleeve 10 and an optional neck support sling 12 to perform various simultaneous non-invasive on invasive health-care related measurements for use in the home, workplace, recreational, clinic or hospital environment. The invention has the advantage over other methods of sensor applications in that no prior knowledge of proper sensor placement is required and that proper placement of the sensors on the patient is assured. The sensor position is stable and reproducible. The invention improves the repeatability of measurements by insuring that the placement and distances between the various sensors remain constant. Moreover, the interplay between the various sensors can result in the combination of data acquisition integration and analysis adding major sophistication and improvement as compared to the individual use of each measuring devices.

In further review, the glove/sleeve 10 together with the optional neck support sling 12 contains one or more of the following measuring elements:

1. An optical emitter and detector 36 attached to the index finger of the glove 10 for the purpose of measuring the level of oxygen saturation in the blood, and peripheral pulse (FIG. 2).
2. A finger plethysmograph device 38 for continuous, beat to beat, noninvasive arterial blood pressure measurement (calibrated by the mean of the arterial blood pressure determinations derived from both the wrist and arm NIBP devices ) (FIG. 2).
3. Inflatable cuff and pressure cuffs or sensor 16, 18 located in various locations on the arm and hand to measure brachial radial or finger blood pressure for periodic (automatic or manual) noninvasive blood pressure measurements (NIBP). These NIBP measuring devices are also used to calibrating the optical system used to measure continuous, beat to beat arterial blood pressure as above mentioned (FIG. 2).
4. A central control unit 24 for the acquisition and transmission of the various biosignals derived from the glove sensors. This central control unit 24 which can be activated locally by the patient or remotely by a monitoring center allows for automatic or manual activation of any or all of the sensors. The central control unit 24 provides amongst other: the initial and repeated sensor calibration procedures, activation of a built-in miniature pump for the creation of positive and negative pressures, the reception of commands from the remote control center, analog to digital conversion of measured data and their transmission to the control center as well as any other needed control functions (FIG. 2).
5. A set of electrodes 30 (V1, V2, RA, RL) placed on the palmar aspect of the glove 10 and/or the neck support sling 12 for the purpose of simultaneous recording of a twelve-lead electrocardiogram (FIG. 3).
6. A method for automatic administration of an electric conductor solution/cream to the electrodes 30 to reduce skin resistance and improve ECG relating quality.
7. A method of producing and maintaining a sufficient negative pressure (suction) inside the ECG electrodes 30 to insure proper contact between the ECG electrode and the skin (FIG. 3).
8. A method of insuring proper contact between the ECG electrodes 30 and the skin by the application of an air cushion or a gel cushion around areas of the glove that are in contact with the skin. The cushion is used to provide a body contour fit (FIG. 3).
9. A method such as a buckle connection 15 to adjust the sling 12 to ensure that the arm is held at the proper level for accurate placement of the ECG electrodes 30 on the patients body.
10. A temperature sensor 40 placed in appropriate areas of the glove/sleeve 10 for the purpose of measuring body temperature (FIG. 4).
11. An electrode or set of electrodes 46 placed in the palm area of the glove for the purpose of measuring skin resistance (FIG. 4).
12. An electronic stethoscope for the auscultation of lungs, heart and other organs.
13. Built-in measuring devices 80 in FIG. 4 in the glove fingers for the accurate assessment of tremor and other normal or neurological forms of finger motions.
14. Built in measuring devices 80 in the glove 10 for the determination of EMG.
15. Built-in measuring devices 80 in the glove 110 for the determination of nerve conduction.
16. Built-in measuring device 82 for the determination of muscle force (hand grip, extension, flexion, etc.).
17. Built-in device 82 for the assessment of rapid/accurate voluntary hand movement.
18. The advised positioning of the patient's left arm on the chest to ensure proper localization of the 12 lead ECG electrodes of the glove for accurate and reproducible 12 lead ECG recording is shown in FIG. 5. This arm position, aided by the adjustable neck support sling 12, is natural and comfortable and therefore allows for prolonged, stable and continuous monitoring of all available parameters (FIG. 5).

Figure 6:
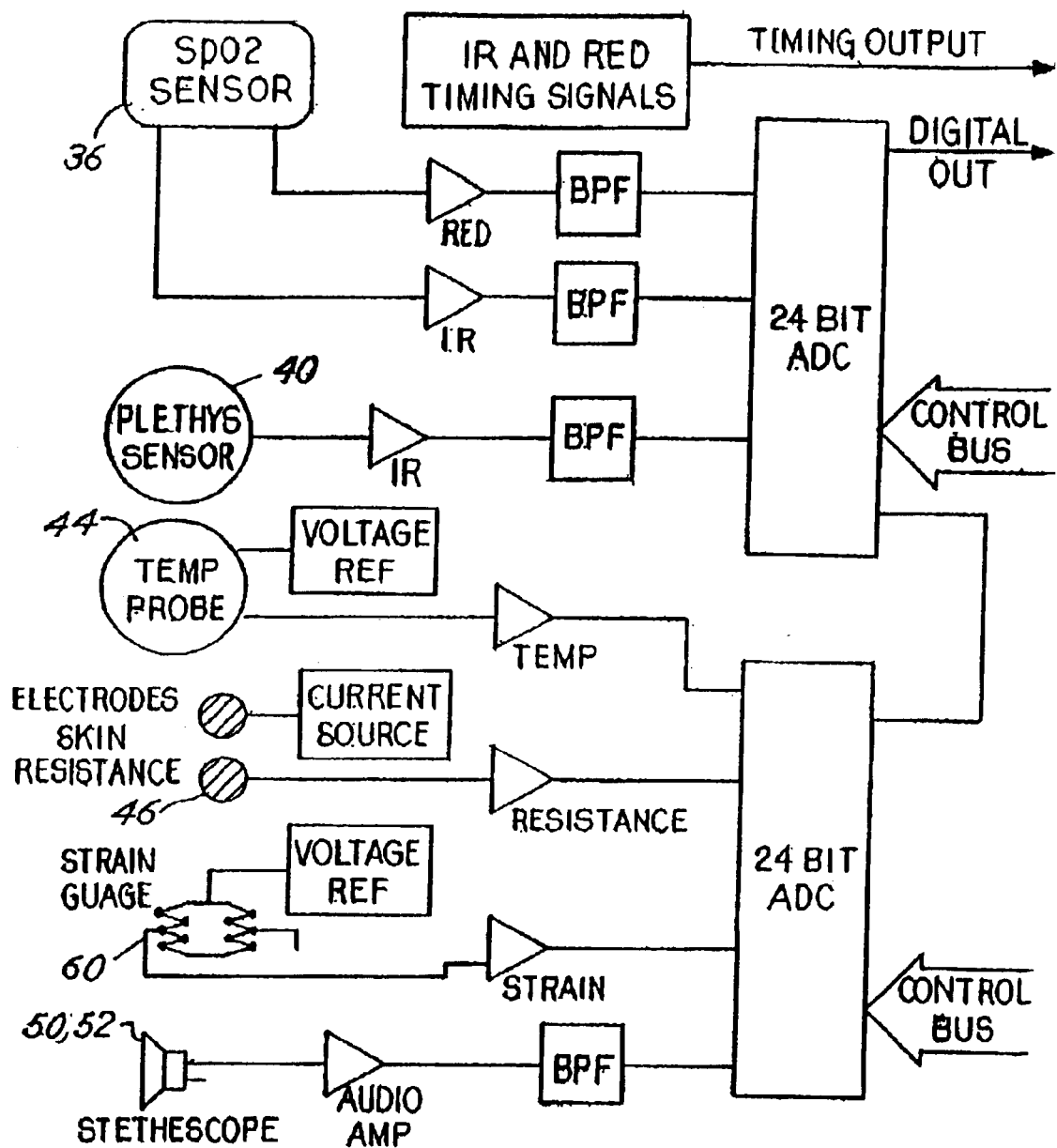
FIG. 6 is a schematic circuit diagram of sensor inputs for the system.

FIGS. 6, 7, 8 and 9 are schematic drawings depicting the basic elements described above. FIG. 6 depicts the various sensors including the Sp02 sensor 36, the plethysmography sensor 38, the temperature sensor 44, skin resistance probes 46, strain gauges 48, and stethoscope sensors 50, 52. As depicted in FIG. 6, each of the inputs in amplified and, if necessary, filtered prior to being converted to a 24 bit analog to digital converter. The output of the analog to digital converter goes via a control ASIC depicted in FIG. 9 to a dual port ram also in FIG. 9 where it is processed and transmitted by a microprocessor and an infrared communications to a stationary unit.

Figure 7:
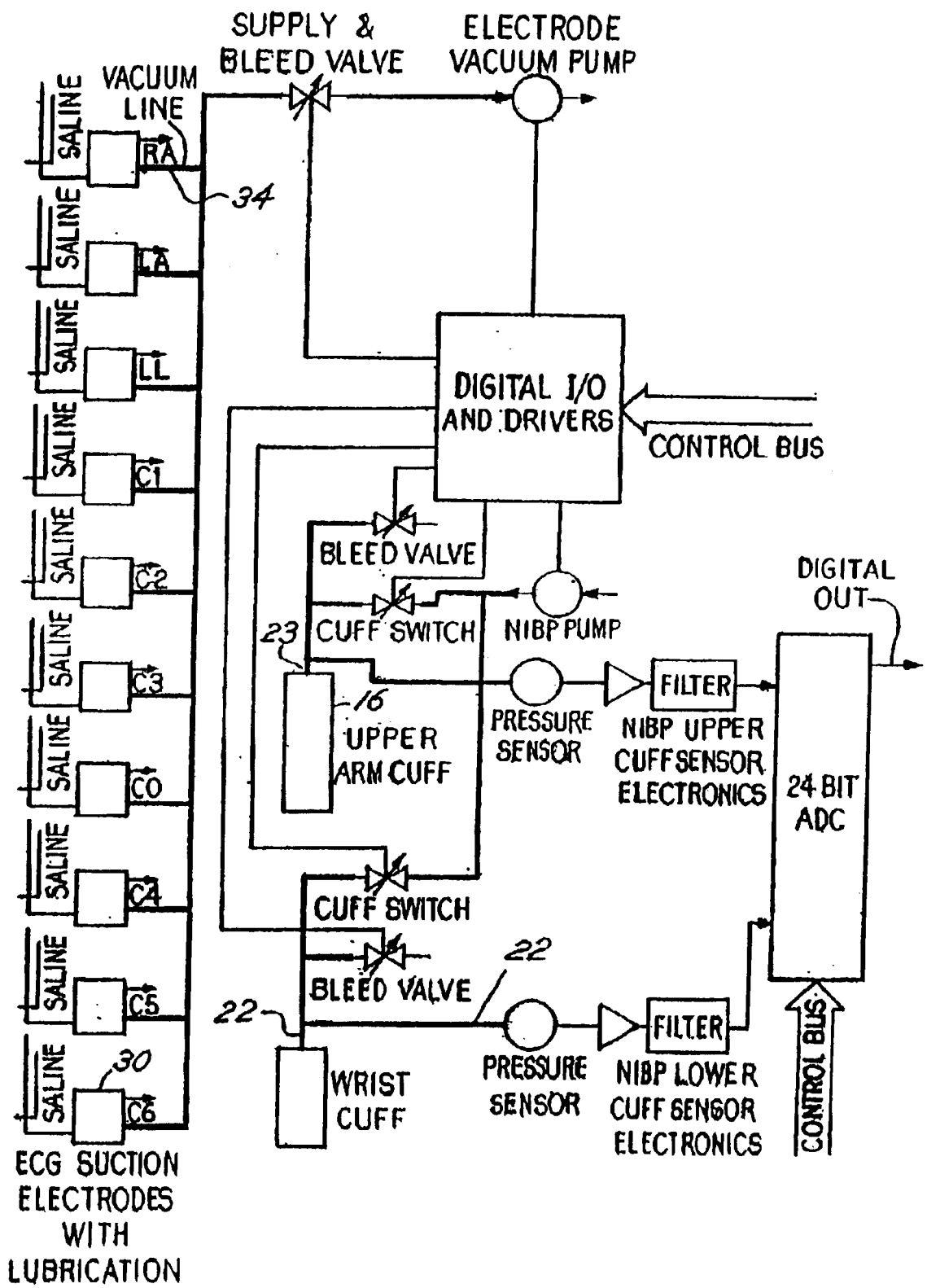
FIG. 7 is a schematic mechanical system diagram of the ECG inputs and blood pressure inputs.

FIG. 7 depicts the various mechanical elements and connections for the ECG electrodes and the blood pressure mechanical and electronic portion of the system. Each ECG electrode comprises a container that holds a saline solution or another lubricant. This solution is drawn into the electrode via a vacuum system. A bleed valve closes the system and then releases the vacuum. The release of the vacuum will then release the lubricant or solution. Digital input output drivers control the vacuum pump and the bleed valve in response to signals that are provided from the ASIC control lines. In the embodiment disclosed, there are two blood pressure cuffs, one associated with the wrist and one with the upper arm. A blood pressure pump (NIBP pump) pumps each cuff. A pressure sensor then measures the pressure in each cuff. The values from the pressure sensor are amplified, filtered and converted to digital values in the 24-bit analog to digital converter. The output of the analog to digital converter also passes through the control ASIC in FIG. 9 to the dual port random access memory unit where it is processed and transmitted by the microprocessor and IR communications, for example, to a stationary unit.

Figure 8:
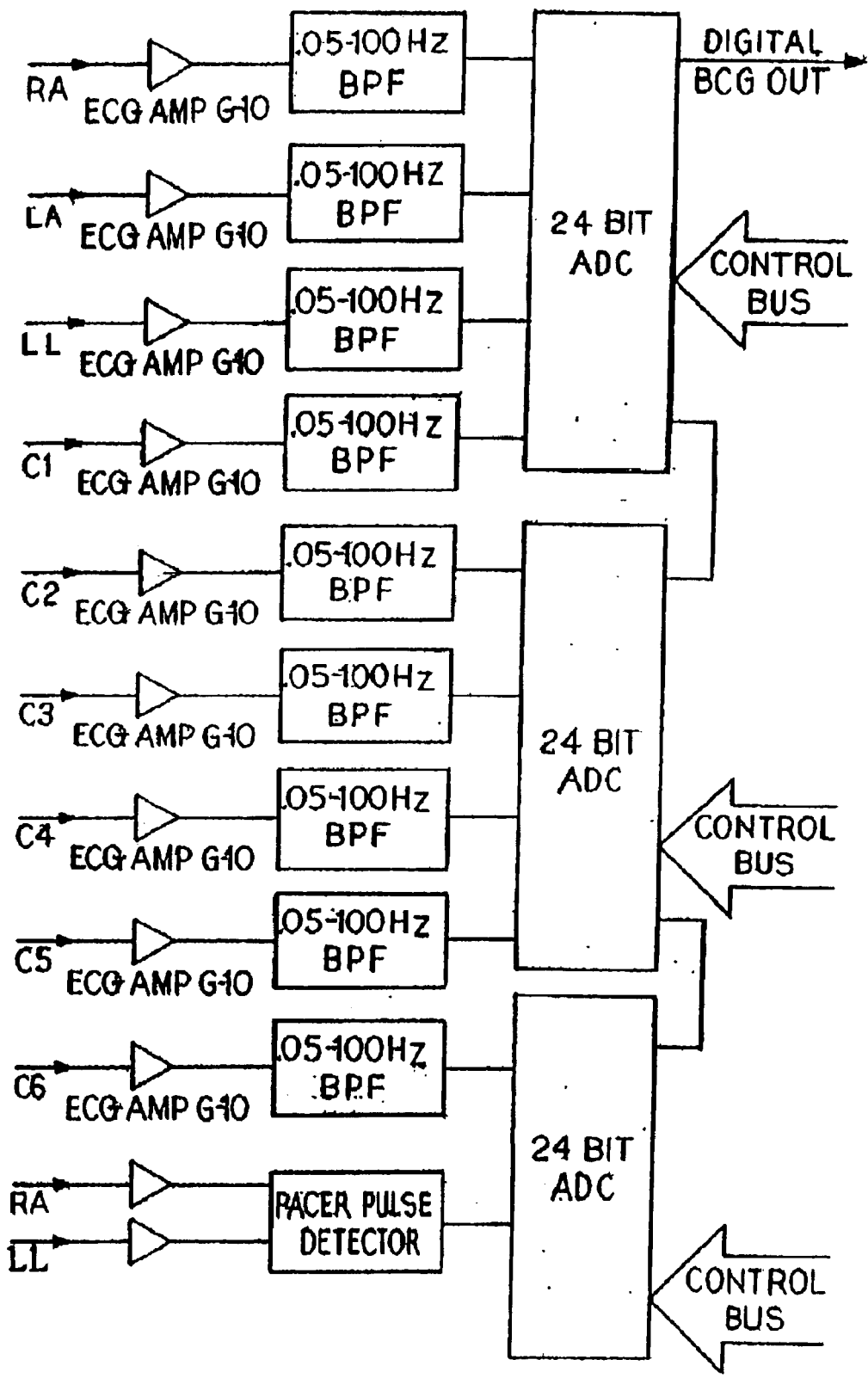
FIG. 8 is a schematic circuit diagram of the input circuitry for the ECG measurements.

FIG. 8 depicts the ECG analog input circuitry. Each electrode input is separately amplified and ban passed filtered prior to conversion by a 24-bit analog to digital converter. The analog to digital converter signal passes through the control ASIC in FIG. 9 to the dual port RAM where it is processed and transmitted again by the microprocessor and IR communications to a stationary unit.

FIG. 9 depicts the digital circuitry in the system. The circuitry includes the ASIC which has logic for the timing signals and for transmitting or passing the digitized analog signals from the various analog to digital converters to the dual port RAM which sits on the microprocessor. The microprocessor runs the software provided from the flash memory, collects data samples, performs basic analysis, controls the various valves and pumps and sends data to the central data collector via IR communication. The described circuitry is but one way to accomplish the goals and objectives of the use of the glove and/or sleeve of the invention.

Variations of the described combination are possible within the spirit and scope of the invention which is to be limited only by the following claims and equivalents thereof.

What is claimed is:

1. A diagnostic garment for obtaining human electrocardiogram (ECG) input readings comprising, in combination:
   a sleeve member for the left hand and arm of a person, said sleeve member having an inside palm side with a hand portion and an arm portion, said sleeve member including electrodes for a multiple lead electrocardiogram (ECG), said sleeve member including RA, RL, V1, V2, V3, V4, V5, V6, LL and LA electrodes on the inside palm side and arm portion arranged to position said electrodes against the chest and torso of a human in the classic chest positions when the left arm is supported with the elbow against the body and the left forearm directed toward the right shoulder.

2. The garment of claim 1 further including a blood pressure cuff in the sleeve.

3. The garment of claim 1 wherein said arm portion of said sleeve includes an upper arm section and further including a blood pressure cuff in the upper arm section of the sleeve.

4. The garment of claim 1 further including a central control unit mounted on the sleeve arm portion for controlling the electrodes and recording readings from eletrodes, said control unit including wireless transmission means for transferring readings.

5. The combination of claim 1 further including means for ejecting an ream into the electrodes.

* * * * *